(12) United States Patent
Marritt

(10) Patent No.: US 6,770,756 B1
(45) Date of Patent: Aug. 3, 2004

(54) PROCESS FOR THE MANUFACTURE OF POLYGULURONIC ACIDS

(75) Inventor: William Alan Marritt, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 490 days.

(21) Appl. No.: 09/357,393

(22) Filed: Jul. 20, 1999

(30) Foreign Application Priority Data

Jul. 21, 1998 (JP) .......................................... 10/205025

(51) Int. Cl.$^7$ ................................................ C07H 1/06
(52) U.S. Cl. ...................... 536/127; 536/123; 536/124; 536/128
(58) Field of Search ................................ 536/123, 124, 536/127, 128

(56) References Cited

U.S. PATENT DOCUMENTS

| | | | | |
|---|---|---|---|---|
| 4,689,322 A | | 8/1987 | Kulbe et al. ................... | 514/54 |
| 5,558,973 A | * | 9/1996 | Yamada ....................... | 430/203 |

FOREIGN PATENT DOCUMENTS

GB         962483        7/1964

OTHER PUBLICATIONS

Haug et al., Acta Chem. Scand., 21, 1967.*
Doublier et al., Carbohydrates in Food, pp. 287–289, 1996.*
Tomoko Shimokawa et al. Some properties and action mode of (1→4)-α-L-guluronan lyase from *Enterobacter cloacae* M-1. 1997. Carbohydrate Research 304: 125–132.

Alain Heyraud et al. NMR spectroscopy analysis of oligoguluronates and oligomannuronates prepared by acid or enzymatic hydrolysis of homopolymeric blocks of alginic acid. Application to the determination of the substrate specificity of *Haliotis tuberculata* alginate lyase. 1996. Carbohydrate Research 289: 11–23.
Abstract XP–002128596, based on JP 06 21774 A (1994), 1 page.
A. Haug et al, Acta Chem. Scand., vol. 21 "Studies on the Sequence of Uronic Acid Residues in Alginic Acid", 1967, pp. 691–704.
M. Natsume et al, "Isolation and Characterization of alginate–derived oligosaccharides with root growth–promoting activities", 1994, 187–197.
Y. Yonemoto et al, "Promotion of Germination and Shoot Elongation of Some Plants by Alginate Oligomers Prepared with Bacterial Alginate Lyase", 1993, vol. 75, pp. 68–70.

* cited by examiner

*Primary Examiner*—James O. Wilson
*Assistant Examiner*—Howard V. Owens, Jr.
(74) *Attorney, Agent, or Firm*—Sughrue Mion, PLLC

(57) ABSTRACT

It is the object of the present invention to provide an industrially useful process for the manufacture of polyguluronic acids having degrees of polymerization less than 20 and substantially free of mannuronic acid contamination. Alginate salts of organic bases are quite soluble in aqueous solution, and remain soluble in aqueous solution throughout a hydrolysis reaction in the range of pH values at which the acidic hydrolysis is effected at a reasonably fast rate. Based on this finding, a solution containing 5 wt. % or more of alginic acid prepared by dissolving alginic acid in water by neutralization with an organic base is provided and then hydrolyzed under acidic conditions, followed by selective precipitation of polyguluronic acids under acidic conditions.

7 Claims, 1 Drawing Sheet

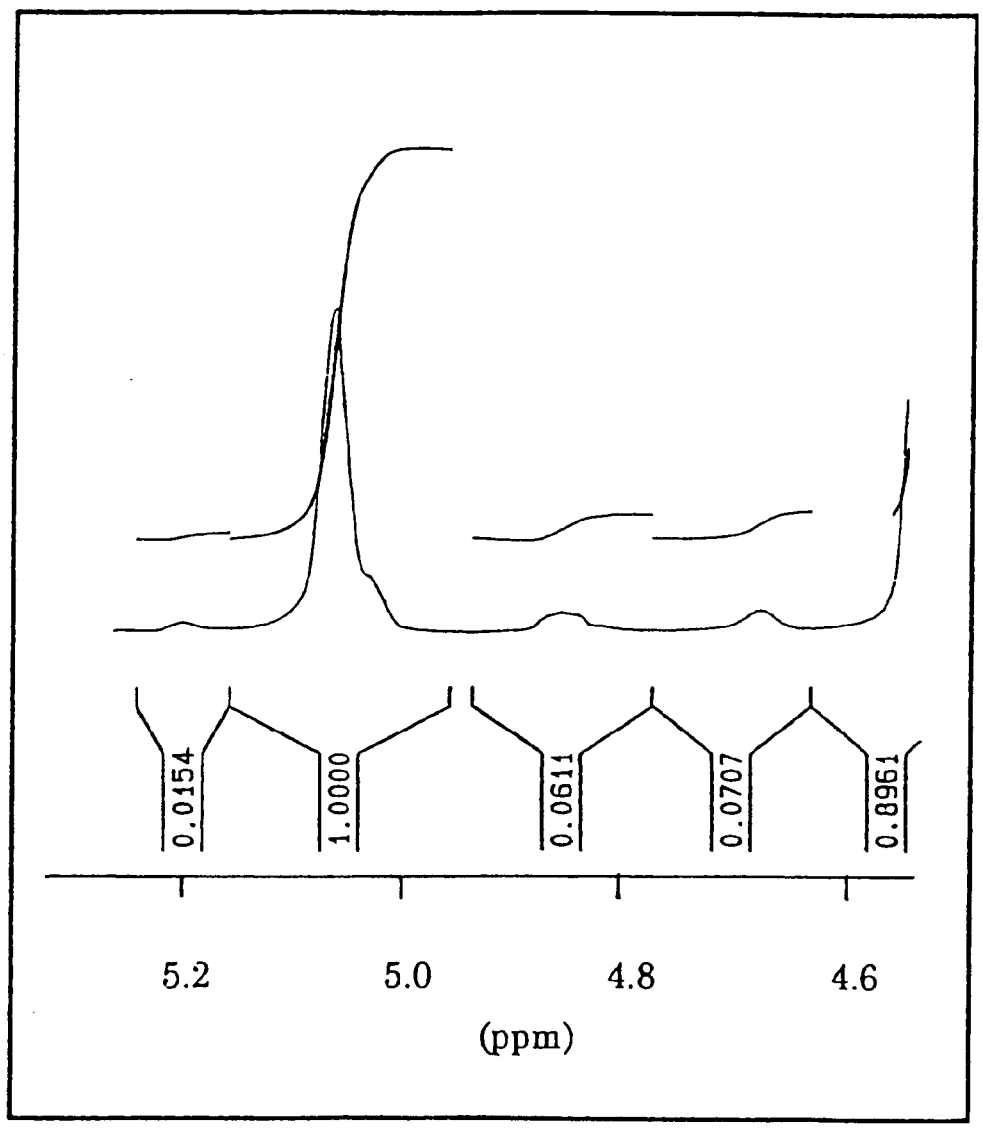
F I G. 1

PROCESS FOR THE MANUFACTURE OF POLYGULURONIC ACIDS

FIELD OF THE INVENTION

The present invention relates to a process for the manufacture of polyguluronic acids having degrees of polymerization less than 20 and substantially free of mannuronic acid contamination.

BACKGROUND OF THE PRESENT INVENTION

Polyguluronic acids, because of their high affinity for calcium ions, are expected to have utility as scale inhibitors and scale deposit removers. The biodegradability of polyguluronic acids makes them particularly valuable with respect to environmental acceptability and waste disposal. Additionally, polyguluronic acid derivatives, in which a hydrophobic polymer is covalently attached to the reducing terminus of the polyguluronic acid, are useful as dispersants in pigment dispersed aqueous ink compositions for use in ink jet printing. Furthermore, polyguluronic acids, having low degrees of polymerization, have been shown to exhibit root-growth promoting activity in barley (M. Natsume et al., "Isolation and Characterization of Alginate-derived Oligosaccharides with Root-Growth Promoting Activities," Carbohydrate Research, 258, 187–197 (1994)). They have also been shown to exhibit germination and shoot-elongation promoting activity in unhulled rice and tobacco callus (Y. Yonemoto et al., "Promotion of Germination and Shoot Elongation of Some Plants by Alginate Oligomers Prepared with Bacterial Alginate Lyase," Journal of Fermentation and Bioengineering, 75, 68–70 (1993)). Based on studies of other polyuronic acids, low molecular weight polyguluronic acids might also be expected to exhibit antiviral, antitumoral, and plant-defense stimulating activities.

Alginic acids, from which polyguluronic acids can be obtained, are unbranched polymers of 1→4 linked α-L-guluronic acid (G) and β-D-mannuronic acid (M) of varying proportions and sequence. A typical structure of an alginic acid molecule may be represented schematically as follows:

As can be seen from the above structure, the distribution of monomers in alginic acid is not random and there is no regular repeat unit. Alginic acids are best described as block copolymers in which there are polyguluronic acid sequences (G-blocks), polymannuronic acid sequences (M-blocks), and sequences containing random arrangements of both guluronic acid and mannuronic acid (MG-blocks).

It is well known that alginates, which are salts of alginic acid, can be hydrolyzed and that the hydrolysis products can be separated to give two predominantly homopolymeric fractions, polyguluronic acid and polymannuronic acid. The most often cited procedure for the preparation of the sodium salt of polyguluronic acid is a heterogeneous acidic hydrolysis method disclosed in A. Haug et al., "Studies on the Sequence of Uronic Acid Residues in Alginic Acid," Acta Chemica Scandinavica, 21, 691–704(1967). The acidic hydrolysis described therein requires that one part of sodium alginate be suspended in twenty parts of 0.3 M hydrochloric acid solution. Because alginic acid is insoluble in the strongly acidic solution, the hydrolysis is a heterogeneous reaction. The heterogeneous mixture is heated for 10+ hours at 100° C. and then the solid is separated from the acidic solution by centrifugation or filtration. After the collected solid is dissolved in water by neutralizing with dilute sodium hydroxide solution, twenty parts of 0.3 M hydrochloric acid solution are added to the solution resulting in reprecipitation of the partially hydrolyzed alginic acid. The resulting heterogeneous mixture is heated for an additional 10+ hours at 100° C. and the solid product is again separated from the acidic solution by centrifugation or filtration. The collected solid is dissolved in water by neutralizing with dilute sodium hydroxide solution and then sodium chloride and water are added to yield a solution which is 0.5 wt. % alginic acid and 0.1 M sodium chloride. An approximately equal volume of 0.025 M hydrochloric acid solution is added to the alginic acid salt solution until a pH value of 2.85 is obtained. The precipitated solid is separated from the acidic solution by centrifugation or filtration. The isolated solid is dissolved in water by neutralizing with dilute sodium hydroxide solution and then precipitated with excess ethanol. The precipitated solid is washed with ethanol, washed with ether, and dried. The sodium salt of the polyguluronic acid prepared by this heterogeneous acidic hydrolysis method has an average degree of polymerization between 15 and 20. The mannuronic acid content is between 5 and 15%, and the yield of product is between 15 and 20%.

During the course of the first step of the heterogeneous acidic hydrolysis, approximately 30% of the alginate goes into solution. An additional 15% of the original alginate goes into solution during the course of the second step. The insoluble fraction which is isolated after both steps contains both polyguluronic acid and polymannuronic acid. In the acidification of the dilute solution containing sodium salts of both polyguluronic acid and polymannuronic acid, polyguluronic acid is selectively precipitated.

Although the heterogeneous acidic hydrolysis method of A. Haug et al. is useful for laboratory scale preparations of polyguluronic acid, it would be difficult to implement on a larger scale, such as that which would be used in industrial production. This is because in the separation step of that method, the concentration of alginic acid is only a very dilute 0.25 wt. %. Additionally, the method has multiple steps and is complicated.

In the same reference as that describing the heterogeneous acidic hydrolysis method, a homogeneous acidic hydrolysis procedure is also reported. In that procedure, a 1 wt. % sodium alginate solution is mixed with an equal volume of a 0.025 M citrate buffer solution such that a combined solution having a pH value of 3.6 is obtained. The solution is boiled at reflux for 5+ hours. Although a method for isolating polyguluronic acids is not reported, presumably a method similar to that used in the heterogeneous acidic hydrolysis method can be used.

Although the homogeneous acidic hydrolysis method of A. Haug et al. may be useful for laboratory scale preparations of polyguluronic acid, it also would be difficult to implement on a larger scale. In that method, the concentration of sodium alginate in the hydrolysis step is only a very dilute 0.5 wt. %. Although one can easily conceive of increasing the concentration of sodium alginate, in practice this cannot be done. At concentrations slightly greater than 0.5 wt. %, sodium alginate does not remain soluble throughout the hydrolysis reaction in the range of pH values at which the acidic hydrolysis is effected. The species which precipitate in the course of the hydrolysis are incompletely hydrolyzed and, although rich in guluronic acid, they contain significant amounts of mannuronic acid. Furthermore, the incompletely hydrolyzed species have degrees of polymerization greater than 20. Because the homogeneous acidic hydrolysis conditions are milder than those described above in the heterogeneous acidic hydrolysis procedure, the incompletely hydrolyzed species are not further hydrolyzed after precipitating from solution.

Thus, there remains a need for a method of manufacturing polyguluronic acids which can be carried out on an industrial scale. Specifically, there remains a need for a hydrolysis process in which the concentration of alginic acid or alginate salt is greater than 5 wt. % throughout the process.

SUMMARY OF THE INVENTION

It is an object of the present invention to provide a practical process for the manufacture of polyguluronic acids having a degree of polymerization less than 20 and substantially free of mannuronic acid contamination.

The present inventor has found that alginate salts of organic bases are quite soluble in aqueous solution. Furthermore, the present inventor has found that these salts remain soluble in aqueous solution throughout a hydrolysis reaction in the range of pH values at which the hydrolysis is effected at a reasonably fast rate. The present invention has been made based on such findings.

According to one aspect of the present invention, there is provided a process for the manufacture of polyguluronic acids, having degrees of polymerization less than 20 and substantially free of mannuronic acid contamination, comprising the steps of:
(a) providing a solution containing 5 wt. % or more of alginic acid prepared by dissolving alginic acid by neutralization with an organic base;
(b) hydrolyzing the alginic acid to lower molecular weight components including polyguluronic acids while maintaining the pH of the solution on the acid side of neutrality;
(c) further acidifying the solution to selectively precipitate polyguluronic acids; and
(d) separating the polyguluronic acids from the acidified solution.

BRIEF DESCRIPTION OF THE DRAWING

FIG. 1 is a diagram showing a $^1$H-NMR spectrum (chemical shift=4.6 to 5.2 ppm) of a hydrolyzate obtained in the example described below.

DETAILED DESCRIPTION OF THE INVENTION

Polyguluronic acids obtained by the process of the present invention have degrees of polymerization less than 20 and are substantially free of mannuronic acid contamination. The expression "substantially free of mannuronic acid contamination" as used herein means that the mannuronic acid content is less than about 8 wt. %, and preferably less than about 5 wt. %.

As noted above, homogeneous acidic hydrolysis, in which sodium alginate is used as the starting material, cannot be carried out at concentrations significantly greater than 0.5 wt. %. The situation is similar for other alkali metal salts of alginic acid, including lithium alginate, potassium alginate, rubidium alginate, and cesium alginate, and ammonium alginate. Alginate salts of metals other than alkali metals are insoluble or sparingly soluble in aqueous solution and, thus, cannot be used in a homogeneous acidic hydrolysis.

On the other hand, alginate salts of organic bases are very advantageous in that they are quite soluble in aqueous solution and remain soluble in aqueous solution throughout a hydrolysis reaction in the range of pH values at which the hydrolysis is effected at a reasonably fast rate.

According to a preferred embodiment of the present invention, organic bases usable in the present invention include organic amines (for example, mono-, di- and tri-alkyl (preferably $C_{1-8}$ alkyl, more preferably $C_{1-6}$ alkyl) amines, tetraalkyl (preferably $C_{1-8}$ alkyl, more preferably $C_{1-6}$ alkyl) ammonium hydroxides, and aromatic amines), tetraarylphosphonium hydroxide, tetraarylarsonium hydroxide, and tetraarylstibonium hydroxide.

According to a preferred embodiment of the present invention, the organic base has a relatively low molecular weight for two reasons. First, low molecular weight organic bases are appreciably soluble in water even before protonation. Second, low molecular weight organic bases yield salts of alginic acid for which the viscosity of an aqueous solution is less than that of a comparable solution prepared using a higher molecular weight organic base.

Examples of organic bases, which can be used in the present invention, include methylamine, dimethylamine, trimethylamine, tetramethylammonium hydroxide, ethylamine, diethylamine, triethylamine, tetraethylammonium hydroxide, n-propylamine, di-n-propylamine, tri-n-propylamine, tetra-n-propylammonium hydroxide, isopropylamine, di-isopropylamine, N-methyl-ethylamine, N-methyl-n-propylamine, N-methyl-isopropylamine, N,N-dimethyl-ethylamine, N,N-dimethyl-n-propylamine, N,N-dimethyl-isopropylamine, N,N-diethyl-n-propylamine, N,N-diethyl-isopropylamine, N,N-di-n-propyl-isopropylamine, N-ethyl-n-propylamine, N-methyl-diethylamine, N-ethyl-di-n-propylamine, N-ethyl-di-isopropylamine, N-propyl-di-isopropylamine, N-methyl-N-ethyl-n-propylamine, N-methyl-N-ethyl-isopropylamine, N-methyl-N-n-propyl-isopropylamine, N-ethyl-N-n-propyl-isopropylamine, monoethanolamine, diethanolamine, triethanolamine, N-methyl-monoethanolamine, N,N-dimethyl-monoethanolamine, N-ethyl-monoethanolamine, N,N-diethyl-monoethanolamine, N-methyl-N-ethyl-monoethanolamine, N-methyl-diethanolamine, N-ethyl-diethanolamine, morpholine, N-methyl-morpholine, N-ethyl-morpholine, imidazole, N-methyl-imidazole, pyridine, 2-picoline, 3-picoline, 4-picoline, tetraphenylphosphonium hydroxide, substituted tetraphenylphosphonium hydroxide, tetraphenylarsonium hydroxide, substituted tetraphenylarsonium hydroxide, tetraphenylstibonium hydroxide, and substituted tetraphenylstibonium hydroxide. According to a preferred embodiment of the invention, the family of methylamines—methylamine, dimethylamine, trimethylamine, and tetramethylammonium hydroxide—are used because the viscosities of the resulting solutions of alginic acid salts are relatively low.

The alginic acid to be used as a starting material in the present invention may be any alginic acid. Further, any commercially available alginic acid may be used. Because polyguluronic acid is the target product, an alginic acid, which is rich in guluronic acid, is preferred. For example, alginic acids extracted from the seaweeds *Laminaria hyperborea* and *Lessonia flavicans* are particularly rich in guluronic acid, having guluronic acid to mannuronic acid ratios of approximately two to one.

According to a preferred embodiment of the present invention, for the purpose of keeping the viscosity of the hydrolysis solution relatively low, an alginic acid having a low average molecular weight is preferred as a starting material. According to a preferred embodiment of the present invention, an alginic acid having a molecular weight of less than or equal to 50,000 g/mole is used. Sodium salts of alginic acid having average molecular weights of 10,000 g/mole are at present commercially available from Kimitsu Chemical Industries (Product Name: ULV-L1G) and Fuji Chemical Industries (Product Name: Snow Algin ULV-S1). A particularly useful alginic acid starting material can be readily obtained by acidifying to a pH value of 2 or less a solution of either of these sodium salts and then collecting the solid by filtration or centrifugation.

As the first step in the present invention, the alginic acid is dissolved in water by neutralization with an organic base to yield a solution containing 5 wt. % or more of alginic acid. A slight excess of organic base may be used to effect the neutralization with the pH of the resulting solution being in the range of about 5 to about 9. For commercial grades of alginic acid, the resulting solution will generally contain small amounts of insoluble impurities which can be easily removed by filtration prior to the acidic hydrolysis step.

In the next step, the alginic acid is hydrolyzed to low molecular weight components including polyguluronic acids. The hydrolysis is carried out under acidic conditions, preferably with heating. The pH value is preferably in the range of 3.2 to 5.0, more preferably in the range of 3.5 to 4.2. This acidity may be realized by the addition of any water-soluble acid, and examples of preferred acids usable herein include hydrochloric acid and lactic acid. According to the process of the present invention, preferably, the pH value of the solution is continuously adjusted during the hydrolysis. This is because it has been found that the pH of the solution increases gradually during the course of the hydrolysis. Although the reason for this gradual increase in pH has not be investigated, presumably it is due to decomposition of the hydrolyzed mannuronic acid fragments, possibly by decarboxylation. Adjustment of the pH can be carried out through the use of commercially available metering devices. According to a preferred embodiment of the present invention, such devices use a pH electrode as a sensor to provide feedback to one or more syringe pumps, which add acid or base to maintain the pH of the solution at a set value.

A temperature of 80° C. or above is preferred for carrying out the hydrolysis reaction. Although temperatures less than 80° C. may be used, the rate of hydrolysis will be correspondingly slower. The hydrolysis reaction may also be carried out in pressure vessels, such that temperatures greater than the boiling point of water may be used. A temperature of less than about 120° C. is preferred because nonselective decomposition of the polysaccharide products, in competition with the hydrolysis reaction, is significant at temperatures greater than about 120° C.

The hydrolysis step may be carried out under an ambient atmosphere or an inert atmosphere, with an inert atmosphere being preferred because air oxidation of the products will be minimized. An inert atmosphere of high purity nitrogen is preferred from the standpoint of cost.

According to the process of the present invention, the reaction is allowed to proceed for a time period sufficient to complete the hydrolysis. The time period which is sufficient to hydrolyze the alginic acid to lower molecular weight components including polyguluronic acids depends on several factors. One factor is the temperature of the reaction. A second factor is the initial concentration of the alginic acid. A third factor is the average molecular weight of the starting material alginic acid. A fourth factor is the pH value of the hydrolysis solution. To determine the completeness of the hydrolysis reaction, a variety of analytical techniques may be used. Most simply, the viscosity of the hydrolysis solution may be monitored and the reaction judged to be complete when a stable value is obtained. Alternatively, aliquots of solution may be removed periodically, the polyguluronic acid fraction isolated, and the polyguluronic acid fraction analyzed by a variety of techniques. Useful techniques included $^1$H-NMR, gel permeation chromatography, and low angle light scattering.

After the hydrolysis is judged to be complete, the solution is cooled to ambient temperature and the solution further acidified to yield precipitates of polyguluronic acids. The pH range of the acidification step, in which polyguluronic acids are selectively precipitated, specifically refers to a pH range in which polyguluronic acids are selectively precipitated from polymannuronic acids. According to a preferred embodiment of the present invention, the pH value is preferably in the range of 3.0 to 3.6, more preferably in the range of 3.1 to 3.5. The reported pKa values of polyguluronic acid and polymannuronic acid are 3.65 and 3.38, respectively. Based on this difference, acidification in the pH range of the present invention, results in selective precipitation of polyguluronic acids from polymannuronic acids, which remain in solution. In this pH range, all of the carboxylic acid groups of polyguluronic acid may not be protonated and some organic base salts may coprecipitate with the polyguluronic acid. If this is problematic for the application in which the polyguluronic acid is to be used, the selectively precipitated polyguluronic acid may be isolated, dissolved in water and then reprecipitated by acidification to a pH value less than about 2. The acidification for the precipitation of polyguluronic acid may be realized by the addition of any water-soluble acid. Examples of preferred acids include hydrochloric acid and lactic acid.

After selective precipitation, the polyguluronic acids are separated from the acidified solution by conventional methods. Such methods include filtration and centrifugation. The product may then be washed with acidified water and/or an aqueous alcohol solution and then dried by conventional methods.

The polyguluronic acids prepared according to the method of the present invention have degrees of polymerization of less than 20 and contain less than 8% mannuronic acid as determined by $^1$H-NMR. A sample for NMR analysis is prepared by dissolving the polyguluronic acid in deuterium oxide ($D_2O$) by neutralization with a solution of sodium deuteroxide (NaOD) in $D_2O$. At 90° C., the H-1 (internal) peaks of guluronic acid and mannuronic acid in polyuronic acids occur at 5.05 ppm and 4.67–4.70 ppm, respectively, relative to the internal reference standard, sodium 3-(trimethylsilyl)propionate-$d_4$. From the integrated areas of these two peaks, the amount of mannuronic acid impurity in the polyguluronic acid product can be calculated. At 90° C., the H-1 (reducing end) peaks of the α and β anomers of polyguluronic acid and polymannuronic acid occur at 5.21 ppm and 4.84–4.89 ppm, respectively, relative to the internal reference standard, sodium 3-(trimethylsilyl)propionate-$d_4$. From a comparison of the combined integrated areas of the α and β anomer peaks to the combined integrated areas of all the H-1 peaks (α anomer peak, β anomer peak, H-1 (internal) peak of guluronic acid in the polyuronic acid, H-1 (internal) peak of mannuronic acid in the polyuronic acid), the degree of polymerization of the polyguluronic acid product can be calculated.

EXAMPLE

The present invention will be further clarified by the following specific example, though it is not limited to this specific example only.

(1) ALGINIC ACID

Alginic acid used in the following specific example was prepared from a commercial sodium alginate (Kimitsu Chemical Industries; Product Name: ULV-L1G; average molecular weight: 10,000). 200 g of ULV-L1G was dissolved in 1.8 liters of deionized water with stirring. While stirring the solution, concentrated hydrochloric acid was added dropwise which resulted in precipitation of alginic acid. The addition of hydrochloric acid was continued until the pH of the mixture reached a value of 0.90. The mixture was stirred for an additional 4 hours and then set aside to stand for 12 hours. Most of the clear supernatant was discarded and the remaining mixture was filtered through a #2 Whatman filter paper to collect the off-white solid. The solid was air-dried for several days and then further dried under vacuum to a constant weight.

(2) PREPARATION OF POLYGULURONIC ACID 100 g of alginic acid was slurried in 700 mL of deionized water in a 1000 mL beaker. To this slurry was added 150 g of aqueous trimethylamine solution (30 wt. %) with stirring. The mixture was warmed to 40° C. and stirring was continued for 4 hours, at which point the alginic acid had substantially dissolved. The solution was then filtered through a #5 Whatman filter paper to remove a small amount of insoluble impurities. The filtrate was transferred to a two-neck 2 L round bottom flask equipped with a magnetic stir bar. The solution was heated to 90° C. with stirring and then 1 M hydrochloric acid solution was added dropwise to the solution until the pH reached a value of about 3.9, as determined using Hydrion Microfine pH test paper having a range of 2.9 to 5.2. A reflux condenser, to which a nitrogen inlet line and a bubbler were attached, was inserted into one of the necks of the flask and a glass stopper was inserted into the other neck of the flask. The solution was then heated at reflux for 12 hours. During this time period, the pH was periodically sampled through the inlet which was closed with the glass stopper and 1 M hydrochloric acid solution was added as needed to maintain the pH of the solution at a value of about 3.9. After this 12 hour reflux, the pH was further reduced to a value of about 3.8 by the dropwise addition of 1 M hydrochloric acid solution. The solution was then heated at reflux for an additional 12 hours. During this time period, the pH was periodically sampled through the inlet which was closed with the glass stopper and 1 M hydrochloric acid solution was added as needed to maintain the pH of the solution at a value of about 3.8. After this 12 hour reflux, the pH was further reduced to a value of about 3.7 by the dropwise addition of 1 M hydrochloric acid solution. The solution was then heated at reflux for an additional 12 hours. During this time period, the pH was periodically sampled through the inlet which was closed with the glass stopper and 1 M hydrochloric acid solution was added as needed to maintain the pH of the solution at a value of about 3.7. The solution was allowed to cool to room temperature and then acidified to a pH value of 3.3 using 1 M hydrochloric acid solution. The mixture was set aside for 12 hours during which time the solid polyguluronic acid settled to the bottom of the flask. The pH value was measured again and additional 1 M hydrochloric acid was added in order to readjust the pH value to 3.3. The solid was collected by vacuum filtration on a fine porosity fritted glass filter and then washed several times with 50 wt. % aqueous methanol solution. The solid was further washed with several portions of methanol and then set aside to air dry. Finally, the solid was dried under vacuum to a constant weight. The yield of product was 19.5 g. Approximately 10 mg of sample was dissolved in 0.4 mL of deuterium oxide by addition of a small amount of sodium deuteroxide in deuterium oxide using a microsyringe. The $^1$H-NMR spectrum was measured at 80° C. and the peaks corresponding to the H-1 (internal) peak of guluronic acid in polyuronic acids, the H-1 (internal) peak of mannuronic acid in polyuronic acids, the H-1 (reducing end) peak of the α anomers, and the H-1 (reducing end) peak of the β anomers were integrated. The integration values are given in Table 1 as shown below. This region of the spectrum is shown in FIG. 1.

TABLE 1

| Proton | Chemical Shift (ppm) (vs. Sodium 3-(trimethylsilyl)-propionate-$d_4$) | Integration Value |
|---|---|---|
| H-1 (internal) of mannuronic acid | 4.67 to 4.70 | 0.0707 |
| H-1 (reducing end) of β anomers | 4.84 to 4.89 | 0.0611 |
| H-1 (internal) of guluronic acid | 5.05 | 1.0000 |
| H-1 (reducing end) of α anomers | 5.21 | 0.0154 |

The amount of mannuronic acid impurity in the polyguluronic acid product was calculated from the integration values for the H-1 (internal) peaks of guluronic acid and mannuronic acid. The calculation is as follows:

$$\text{mannuronic acid impurity } (\%) = 100 \times 0.0707/(0.0707 + 1.0000)$$
$$= 6.6\%$$

The degree of polymerization of the polyguluronic acid product was calculated from the combined integrated areas of the α and β anomer peaks and the combined integrated areas of all the H-1 peaks (α anomer peak, β anomer peak, H-1 (internal) peak of guluronic acid in polyuronic acid, H-1 (internal) peak of mannuronic acid in polyuronic acid). The calculation is as follows:

$$\text{degree of polymerization} = (0.0707 + 1.0000 + 0.0611 + 0.0154)/(0.0611 + 0.0154)$$
$$= 15$$

What is claimed is:

1. A process for producing polyguluronic acids, having degrees of polymerization less than 20 and substantially free of mannuronic acid contamination, comprising the steps of:
    (a) providing a solution containing 5 wt. % or more of alginic acid prepared by dissolving alginic acid by neutralization with an organic base;
    (b) hydrolyzing the alginic acid to lower molecular weight components including polyguluronic acids while maintaining the pH of the solution on the acid side of neutrality;

(c) acidifying the solution to selectively precipitate polyguluronic acids; and (d) separating the polyguluronic acids from the acidified solution.

2. The process of claim 1 wherein the organic base is an organic amine, tetraarylphosphonium hydroxide, tetraarylarsonium hydroxide, or tetraaryl stibonium hydroxide.

3. The process of claim 2 wherein the organic base is selected from the group consisting of methylamine, dimethylamine, trimethylamine, tetramethylammonium hydroxide, and mixtures thereof.

4. The process of any one of claims 1 to 3, wherein the hydrolysis is carried out at pH 3.2 to 5.0.

5. The process of any one of claims 1 to 3, wherein the hydrolysis is carried out at a temperature of 80° C. or above.

6. The process of any one of claims 1 to 3, wherein the precipitation of polyguluronic acids is carried out at pH 3.0 to 3.6.

7. The process of any one of claims 1 to 3, wherein the molecular weight of alginic acid is not more than 50,000 g/mole.

* * * * *